Figure 1:
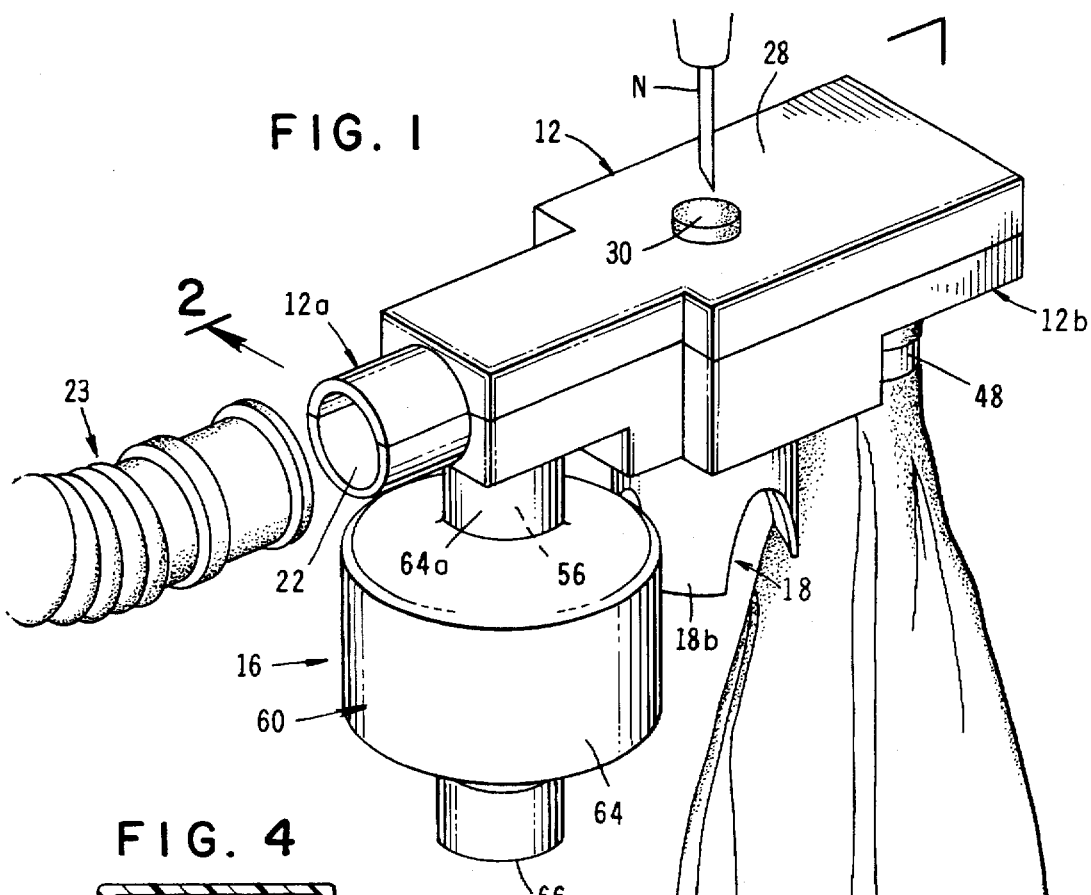
Figure 4:
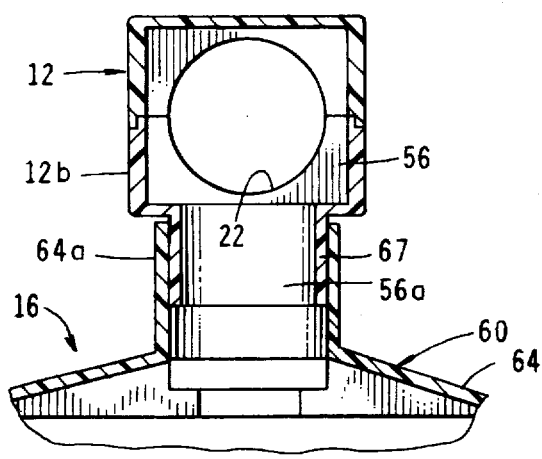
Figure 5:
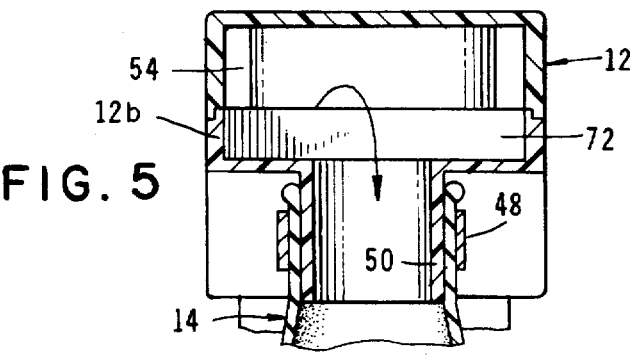

United States Patent [19]

King

[11] Patent Number: 5,752,502
[45] Date of Patent: May 19, 1998

[54] GENERAL PURPOSE AEROSOL INHALATION APPARATUS

[76] Inventor: Russell Wayne King, 1220 Via Granate, Sierra Madre, Calif. 91024

[21] Appl. No.: 167,157

[22] Filed: Dec. 16, 1993

[51] Int. Cl.$^6$ ............................................. A61M 16/00
[52] U.S. Cl. ...................... 128/200.18; 128/200.21; 128/203.12; 128/205.12; 128/203.28
[58] Field of Search .................. 424/45; 128/203.28, 128/200.23, 203.12, 203.14, 203.21, 203.22, 207.14, 205.13, 204.25, 200.21, 205.12, 200.18

[56] References Cited

U.S. PATENT DOCUMENTS

| | | |
|---|---|---|
| 3,967,619 | 7/1976 | Story et al. . |
| 4,484,577 | 11/1984 | Sackner et al. ............... 128/200.23 |
| 4,534,343 | 8/1985 | Nowacki et al. ............... 128/203.15 |
| 4,790,305 | 12/1988 | Zoltan et al. ............... 128/203.28 |
| 4,823,784 | 4/1989 | Bordoni et al. . |
| 4,926,852 | 5/1990 | Zoltan et al. ............... 128/203.24 |
| 5,020,530 | 6/1991 | Miller . |
| 5,027,806 | 7/1991 | Zoltan et al. ............... 128/203.28 |

*Primary Examiner*—Raj Bawa
*Attorney, Agent, or Firm*—James E. Brunton

[57] ABSTRACT

An apparatus for use in respiratory therapy procedures in the field of medicine. The apparatus of the invention converts liquid medication into an aerosol mist comprising submicron size particles and provides for delivery of this mist with such high efficiency that up to 40% of the original dose of medication placed in the nebulizer will be deposited in the patient's lungs.

12 Claims, 4 Drawing Sheets

U.S. Patent — May 19, 1998 — Sheet 1 of 4 — 5,752,502

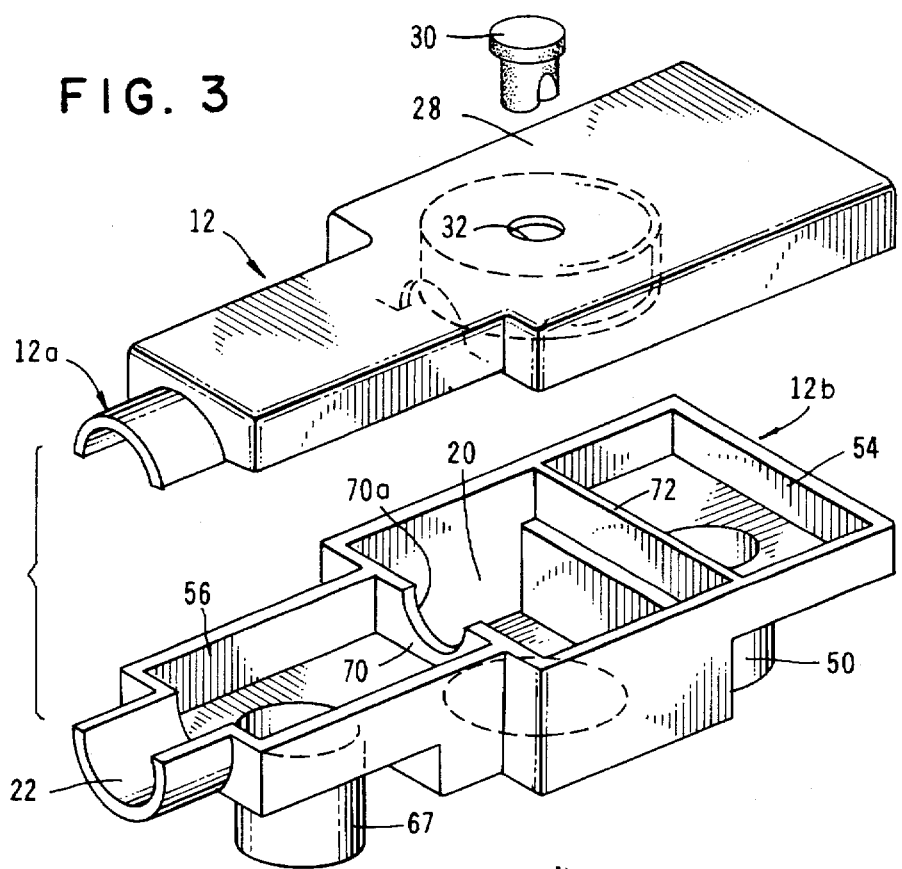
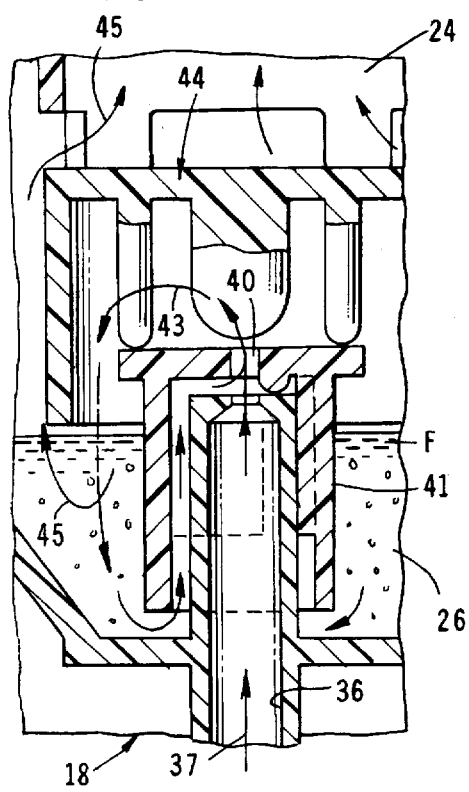
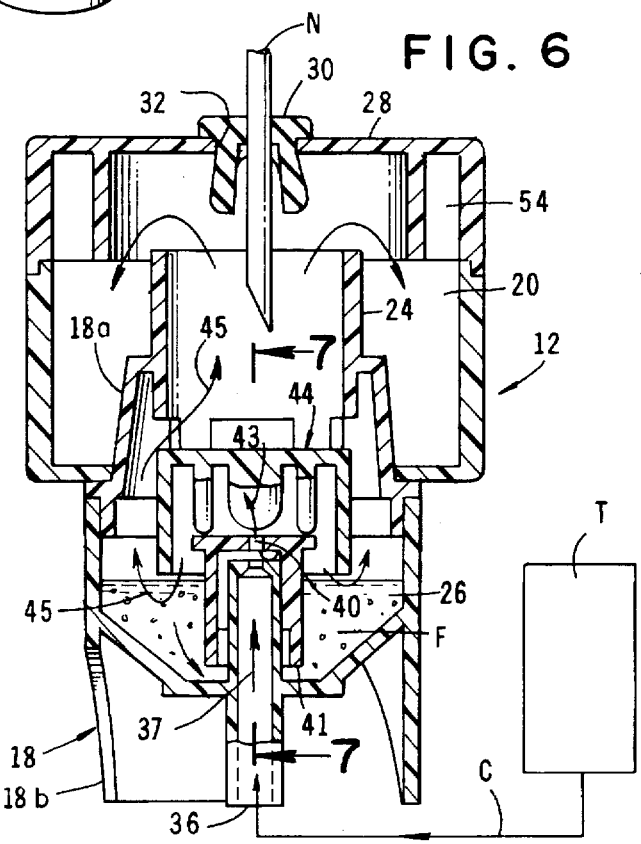

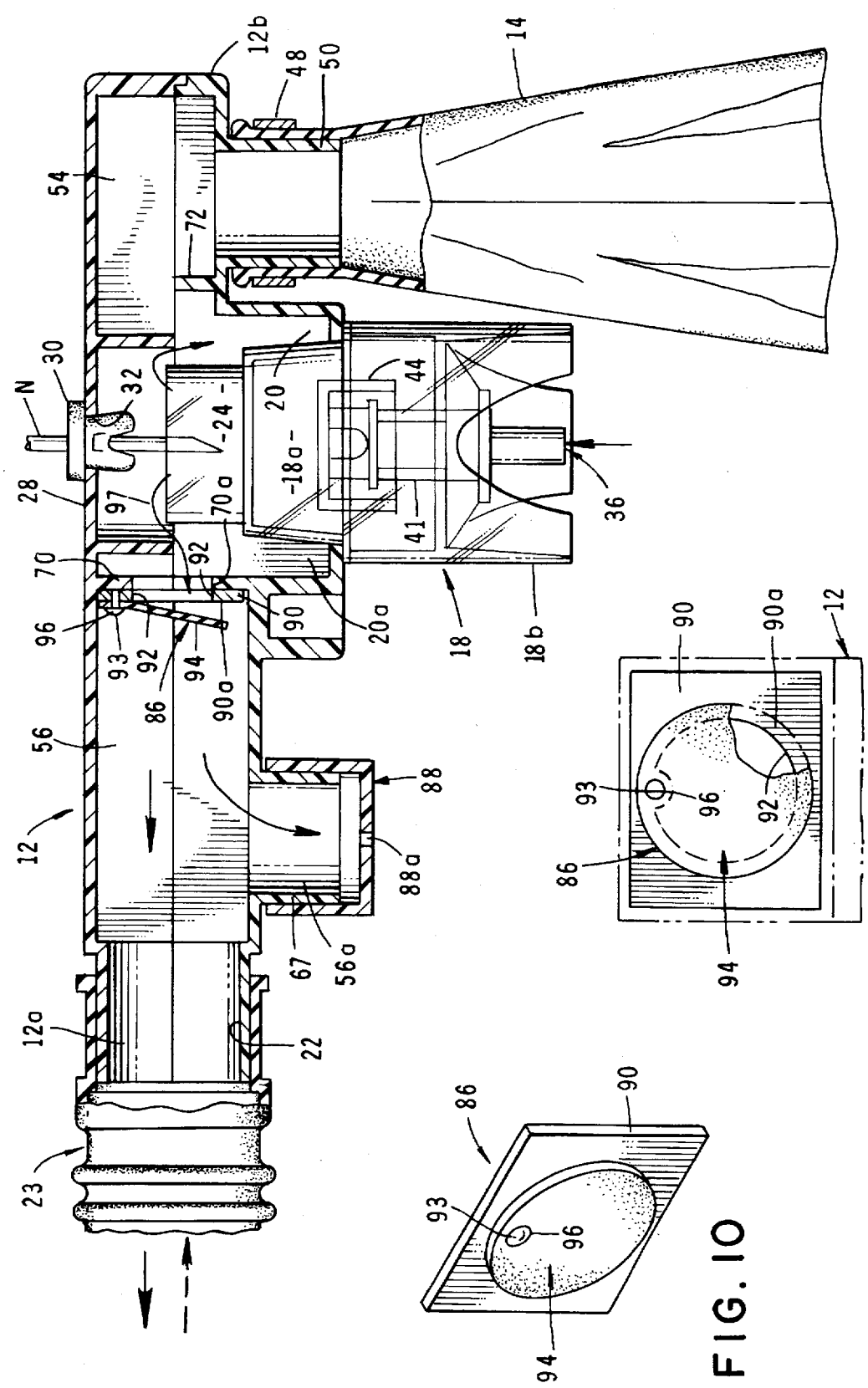

GENERAL PURPOSE AEROSOL INHALATION APPARATUS

BACKGROUND OF THE INVENTION

1. Field of the Invention

The present invention relates generally to inhalation devices. More particularly, the invention concerns an improved aerosol inhalation apparatus for medicinal use that delivers a mist of properly sized aerosol particles of medicament to the patient with a very high-level of efficiency.

2. Discussion of the Prior Art

Therapeutic aerosols are commonly administered to patients suffering from numerous type of pulmonary diseases. Specific medications include beta$_2$ agonists, anticholinergies, cromolyn sodium, and steroids. More recently the aerosol method of delivery has been used to administer Pentamidine to patients afflicted with AIDS, and is presently under consideration as a delivery means for use in the treatment of cystic fibrosis using gene therapy. Experience has shown that the use of aerosols to treat lung disease is highly advantageous in that it produces optimal therapy with minimum side effects.

Both physical and clinical factors affect aerosol deposition in the lungs. Physical factors include inertial impaction, sedimentation, and diffusion. Clinical factors include particle size, ventilatory pattern and lung function. Aerosols larger than 5 micron mass median aerodynamic diameter (MMAD) poorly penetrate the upper respiratory tract. Those in the 0.2 to 1 micron range tend to have their maximum deposition in the lung parenchyma.

In general the devices used for producing medical aerosols fall into two categories; the small volume nebulizer (SVM), and the metered dose inhaler (MDI). The small volume nebulizer (SVN) has traditionally been the apparatus of choice for delivery of therapeutic aerosols. The delivery apparatus typically consists of a disposable or reuseable nebulizer, a mouthpiece or facemask, and a pressurized gas source usually oxygen or air. The metered dose inhaler (MDI), on the other hand, typically contains the active drug, a metering valve, and chlorofluorcarbon (CFC) propellents. The drug containing canister of the device is generally fitted to a mouthpiece actuator, and activation by compression of the canister into the mouthpiece results in the release of a unit dose of medication.

As stated in current literature (*Respiratory Care*, vol. 38, No. 38, Aug. 93, and *Advance for Respiratory Care Practitioners Aug.* 9, 1993, pp. 8–10) the most limiting factor in the use of aerosolized medication is the inefficient mist production by current commercial nebulizer systems, whether they are of the small volume nebulizer (SVN) or metered dose inhaler (MDI) variety. Research has shown that most state-of-the-art commercial units deliver less than 10% of the original dose of medication to the patient's respiratory tract. (*Respiratory Care*, vol 38, #8, Aug. 1993, p. 877, and *AARC Times*, Jun. 1993, p. 48.) The apparatus of the present invention provides a very substantial improvement over all existing prior art aerosol devices by increasing the efficiency of delivery of medication to the patient by a factor of 3 to 5 times that exhibited by currently available prior art nebulizer devices. As a further substantial benefit, the apparatus of the present invention functions in a manner to assure that the medicament particles delivered to the patient will be of optimum size for optimum distribution throughout all of the lung area.

SUMMARY OF THE INVENTION

It is an object of the present invention to provide an inhalation apparatus which will deliver an aerosolized medication to the patient which comprises up to 40% of the original dose of medication, this representing a three to five fold increase over presently available prior art aerosol systems.

Another object of the invention is to provide an apparatus of the aforementioned character which provides a mechanism whereby larger particles of medication will be entrapped and only properly sized particles will go forward so that all extremities of the lung area will effectively receive access to adequate medication.

Another object of the invention is to provide a novel inhalation device wherein particulate escape routes to atmosphere are minimized in instances where medication is used that should preferably be closely controlled or contained.

Another object of the invention is to provide an aerosol inhalation apparatus in which the liquid medication to be aerosolized can be easily and safely injected into the aerosol unit using a cannula and syringe.

Still another object of the invention is to provide an aerosol unit which includes a removable breathing tube which extends outward from the unit and terminates in a patient mouthpiece.

Yet another object of the invention is to provide means for safely filtering air exhaled from the patient before its release to room atmosphere.

BRIEF DESCRIPTION OF THE DRAWINGS

FIG. 1 is a generally perspective view of one form of the inhalation apparatus of the invention.

FIG. 2 is an enlarged, cross-sectional view taken along lines 2—2 of FIG. 1.

FIG. 3 is a generally perspective, exploded view of the main housing of the apparatus.

FIG. 4 is a cross-sectional view taken along lines 4—4 of FIG. 2.

FIG. 5 is a cross-sectional view taken along lines 5—5 of FIG. 2.

FIG. 6 is a cross-sectional view taken along lines 6—6 of FIG. 2.

FIG. 7 is an enlarged, cross-sectional view taken along lines 7—7 of FIG. 6.

FIG. 8 is a cross-sectional view of an alternate form of filter for use in connection with the apparatus of the invention.

FIG. 9 is a side elevational view partly in cross section of an alternate form of the apparatus of the invention.

FIG. 10 is a generally perspective view of the one way valve embodied in the apparatus shown in FIG. 9.

FIG. 11 is a front view of the one way valve of FIG. 10, partly broken away to show the valve seat.

DESCRIPTION OF THE INVENTION

Referring to the drawings and particularly to FIGS. 1 and 2, the aerosol inhalation apparatus of one form of the invention can be seen to comprise a sectionalized main housing 12 to which is attached an inflatable bag 14, a bacteria filter 16, and nebulizer means, shown here as a small volume nebulizer (SVN) 18. As best seen in FIGS. 2 and 3, the upper half **18*a* of nebulizer 18 is enclosed within a first chamber 20 of the main housing 12 and the lower half 18*b* is disposed externally for ease of accessibility. A first end 12*a* of the main housing is provided with a standard size breathing port 22** for ready patient interfacing with the aerosol system via a conduit, or breathing tube 23. In a manner presently to be described, the various sections of chambers of the main housing are interconnected by appropriately baffled fluid flow passageways which are constructed and arranged in a manner to maximize the amount of aerosolized medication that is accessed by the patient.

Figures 2, 8:
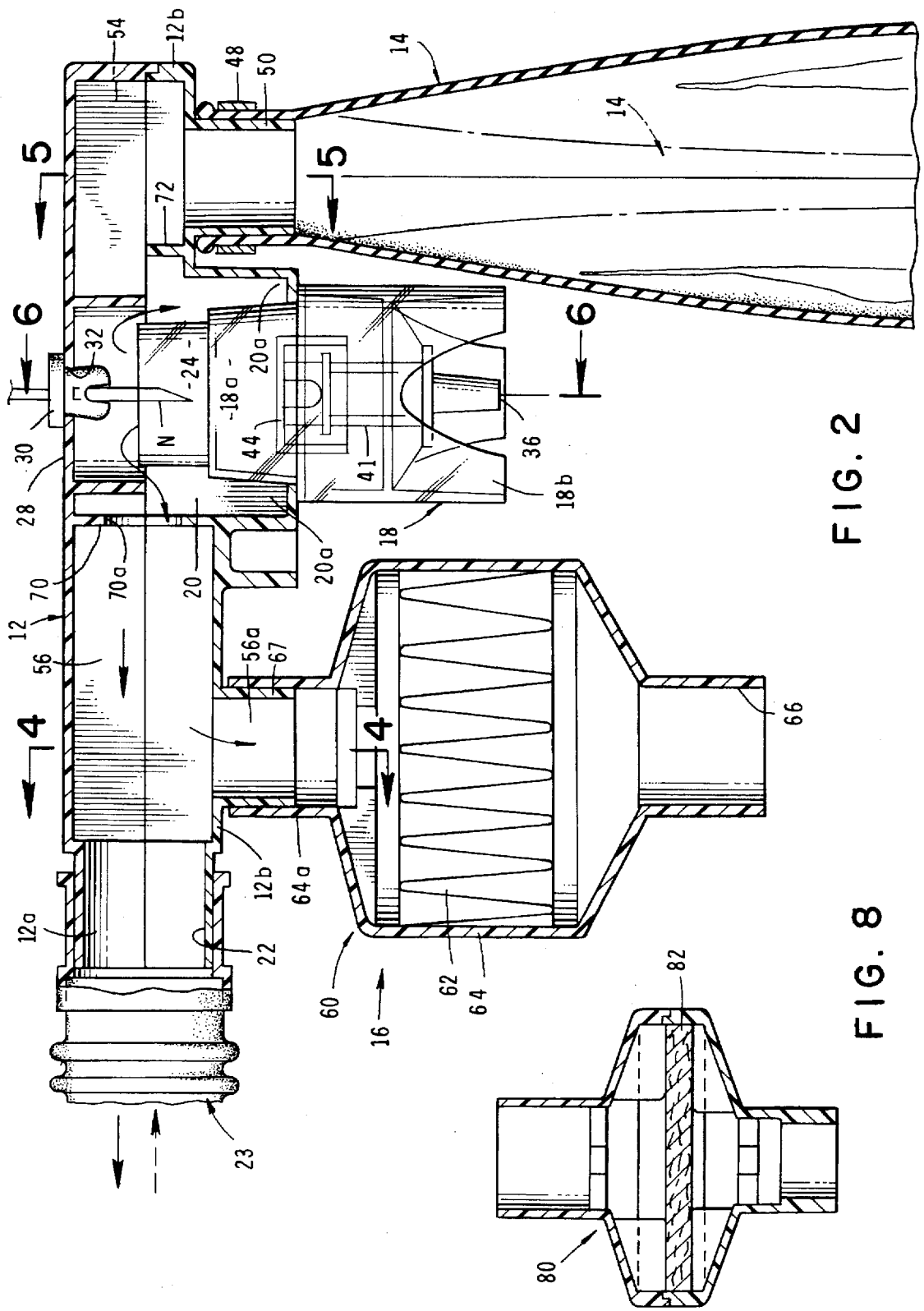

Turning particularly to FIG. 2, the nebulizing means, or nebulizer 18 of the apparatus is mounted partially within first chamber 20 and functions to nebulize a selected fluid medication to produce a fine particle-laden spray having a precise range of sizes of medicament particles contained therewithin. Nebulizer 18 is of a standard construction well known to those skilled in the art, and as indicated in FIGS. 6 and 7, nebulizer 18 includes an upper cylindrical collar 24 and a lower liquid reservoir portion 26.

Carried by a wall 28 of housing 12, which is disposed directly above nebulizer 18, is access means for accessing nebulizer 18 to supply medication fluid to reservoir portion 26 thereof. In the embodiment of the invention shown in the drawings, the accessing means comprises a self-sealing, penetrable septum 30 which, as shown in FIGS. 3 and 6, is sealably mounted within an aperture 32 provided in top wall 28 of housing 12. For certain applications, septum 32 can also comprise a split septum adapted to receive a blunt cannula. Septum 30 is preferably constructed of soft rubber or other suitable elastomer material which is readily penetrable by a blunt cannula or by the needle "N" of a hypodermic syringe (FIG. 6).

Nebulizer 18 also includes a gas inlet means here comprising a gas inlet port 36, which is interconnected with a source of gas under pressure such as a tank "T" (FIG. 6). The nebulizer gas inlet means functions to permit the controlled introduction into the nebulizer of a selected gas under pressure in a manner to cause nebulizing of the fluid disposed within reservoir 26 of the nebulizer. This particulate containing fluid is generally designated in FIG. 6 by the letter "F" and may comprise any of a large number of medications, or mixtures thereof, depending upon the end use to be made of the apparatus.

In operating the nebulizer, the source of gas "T", such as oxygen or compressed air, is interconnected, with inlet 36 by a suitable conduit "C" (see FIG. 6). The gas is preferably supplied to the nebulizer at a flow rate of about ten liters per minute. As best seen in FIGS. 6 and 7, the gas flowing through the inlet port in the direction of the arrow 37 passes through a very small nebulizer orifice 40 provided in a specially configured member 41. This causes the fluid "F" to be drawn from reservoir 26 through orifice 40 in the direction of the arrow 43. Due to the basic design of the nebulizer and in accordance with the Bernoulli effect, the liquid drawn from the reservoir will be predictably converted into a fine mist containing a mixture of particles of varying sizes. After flowing through orifice 40, the fine particulate laden mist will be forced around a flow control member 44 and then upwardly through the nebulizer unit and into collar 24 in the direction of the arrows 45. Flow control member 44, which surrounds the outlet side of orifice 40 in the manner shown in FIG. 6, functions to increase turbulence within the nebulizer and to properly direct fluid flow toward collar 24. This novel construction reduces the size of the particles reaching the outlet port of the device and, along with settling means, the character of which will presently be described, limits the size of the particles that ultimately reach the patient.

As best seen in FIGS. 1 and 2, a reservoir means, shown here in the form of an inflatable bag 14 having a capacity of about two liters, is, secured by a ring clamp 48 to a cylindrically shaped port 50 which is integrally formed with bottom assembly 12b of housing 12. Port 50 communicates with a second chamber 54 which is formed in housing 12 adjacent first chamber 20. Housing 12 is also provided with a third chamber 56 which is in communiction with an outlet port 56a to which there is connected a filtering means for impeding fluid flow through the outlet port and for filtering particles from the spray flowing into chamber 56 as a result of exhalation by the patient through the breathing tube or conduit 23. In the embodiment of the invention here shown, the filtering means comprises a filtering assembly 60 of the character best seen in FIG. 2. Assembly 60 includes a filtering element 62, which is retained within a housing 64, having neck portion 64a, and functions to filter particulates from the fluid flowing from chamber 56 through outlet port 56a, through filtering element 62 and outwardly of port 66 to atmosphere. Neck 64a is closely receivable over a cylindrical skirt 67 which forms a part of housing 12. Filtering element 62 is of a character well known to those skilled in the art and is commercially available from sources such as Intertech of Lincolnshire, Ill.

For so long as compressed air or oxygen is supplied to the nebulizer through inlet 36 and for so long as liquid remains within the nebulizer reservoir, a constant supply of medication containing mist will be supplied to first chamber 20. On average, a patient breathes approximately 10 to 12 times per minute and the adult tidal volume is in the order of 600 to 700 cc. Under normal patient dynamics, an inhalation breath will average approximately one second, and there is a retention time of on the order of one second, followed by an exhalation time of about three seconds. Using conventional small volume nebulizer (SVN) configurations, the patient is accessing aerosolized medication only during the inhalation period of perhaps one second. If the nebulizer is operating at 10 liters/min., during the one second inhalation period the patient will have received only 10,000cc/60 sec.=167cc of aerosolized medication with the remainder of the patient's tidal volume breath being composed essentially of room air. During patient retention and exhalation, the nebulizer output is being vented either through a filter or directly to the atmosphere. Accordingly, normal patient breathing dynamics severely limits the efficiency of conventional nebulizer circuits.

The novel apparatus of the present invention uniquely overcomes the drawbacks of prior art inhalation devices by substantially minimizing the loss of aerosolized medication during the exhalation phase of patient breathing.

As indicated in FIG. 2, during optimum system operations, nebulizer 18 is continually supplying a fine mist of aerosolized medication to first chamber 20 at a rate of approximately 167ccd per second. At the start of the treatment cycle, this mist is inhaled into the patient's lungs through a passageway 70a formed in a wall 70, which separates chambers 20 and 56, and via chamber 56 and conduit 23.

As shown in FIG. 2, first chamber 20 is in communication at all times with second chamber 54 and with third chamber 56 with flow being unobstructed by check valves. During the following three second exhalation period, the expired air pushes a portion of the medication laden mist being generated from chamber 20 into chamber 54 and then into inflatable bag 14, with any excess expired air flowing to atmosphere through filter assembly 60. Uniquely, during the patient's next breath, medication laden mist is inhaled by the patient both from chamber 20 and from inflatable bag 14 in a volume sufficient to fully satisfy the patient's tidal volume requirements. This medication laden mist from chambers 20 and 54, goes into and is distributed through out the patient's lung area. During each subsequent breath, the process is repeated. Absent chambers 54 and inflatable bag 14, which is connected thereto, exhalation by the patient would cause a substantial portion of the medication laden mist being generated to be lost via filter 62 to atmosphere.

In addition to making more medication available to the patient and minimizing medication loss to atmosphere, chambers 20 and 56 also uniquely comprise settling means which function to remove large particles of medicaments from the particulate laden mist by means of sedimentation. In this connection, novel baffling means, of a character presently to be described, promote the effective entrapment of large particles with the result being that the particles actually being accessed by the patient are very small, as for example on the order of 0.3 microns MMAD. These particles are sufficiently small so that they desirably reach the extremities of the lung area through which medication is transported to the blood.

The previously mentioned baffling means of the invention comprise a first baffle means, or wall 72, which separates first and second chambers 20 and 54 as well as a wall 70, which separates first and third chambers 20 and 56. The settling means also comprises a settling chamber 20a which comprises a portion of first chamber 20 (FIG. 2). In operation, wall 72 functions to impede the flow of large particles toward second chamber 54 causing them to fall by force of gravity into settling chamber 20a. Similarly, wall 70 functions to impede the flow of large particles toward third chamber 56, once again causing the large particles traveling toward chamber 56 to fall by force of gravity into chamber 20a.

To vividly demonstrate the high levels of efficiency of the apparatus of the present invention, measurements have been made through use in the nebulizer chamber of radioactive labeled $Tc^{99}M$ DTPA. By sensing emissions from the radioactive particles that are actually deposited in the patients lungs, it has been shown that, if run to dryness, up to 40% of the fluid medication placed in the nebulizer reservoir will be deposited in the patient's lungs.

Turning now to FIG. 8, a filter assembly 80 of alternate construction to filter assembly 60 is there shown. Assembly 80 is receivable over skirt 67d of housing 12 and includes a filtering element 82 of different construction from that in element 62. More particularly, element 82 comprises a generally disk-shaped, relatively dense, porous mass adapted to capture particulate matter contained in the fluid flowing through outlet port 56a. Once again element 82 is of a character well known in the art and is readily commercially available.

Referring now to FIGS. 9, 10 and 11 an alternate form of inhalation apparatus of the present invention is there illustrated. This alternate form is similar in many respects to that shown in FIG. 2 and like numerals have been used to identify like components. A major difference between this latest form of the invention and that of FIG. 2 is the addition of novel valve means here provided in the form of a one way valve assembly 86 of novel construction which is disposed proximate passageway 71a. Another difference is the replacement of filter assembly 60 with a sealing cap 88 the function of which will presently be discribed.

As best seen in FIGS. 10 and 11, valve assembly 86 comprises a base wall 90 having central opening 92 therethrough. Affixed to wall 90 at a single pivot point 93 is a generally circular substantially flexible flapper valve member 94. Valve member 94 can be constructed of a number of materials including plastic and various yieldably deformable elastomeric materials. Pivot point 93 is defined by a fastener such as rivet 96 which passes through member 94 at a location proximate its outer periphery and then through base wall 90 in the manner shown in FIG. 9. With this unique construction, fluid passing through passageway 70 in the direction of the arrow 97 will flow through aperture 92 and will cause valve member 94 to open in a novel pivoting motion about pivot point 93. Conversely, fluid flowing in an opposite direction will cause valve member 94 to securely close and move into sealing engagement with a portion 90a of wall 90 that circumscribes opening 92 thereby blocking fluid flow through passageway 70a.

When the apparatus is in use, patient inhalation will cause the valve to open to permit the aerosolized medication to flow from chamber 20 into chamber 56 and then into the patient's lungs. During the time of patient breath hold and exhalation, the one-way valve will close causing mist produced during this period of time to be retained within chambers 20 and 54, and within the inflatable bag 14. This accumulation will fully satisfy the patient's next breath tidal volume requirements. Once again, this novel construction permits maximum effective use to be made of the particulate laden mist being generated by the nebulizer.

In those situations where no harm results from exhalation of the particulate laden mist directly into the atmosphere, the filter means can be removed and replaced with the less expensive cap 88 which fits securely over cylindrical portion 67. Cap 88 is provided with a small, centrally disposed aperture 88a which permits flow to atmosphere and at the same time provides sufficient impedance to such flow as to insure proper closing of valve member 94 upon patient exhalation.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An aerosol inhalation apparatus for delivering a medicament containing mist to a patient comprising:
   (a) a housing consisting essentially of interconnected first, second and third chambers, said first chamber being in free communication at all times with both said second and third chambers with said free communication being unobstructed by one-way check valves;
   (b) nebulizing means connected to said housing for communication with said first chamber thereof for nebulizing a fluid medication containing the medicament to produce a fine particulate laden spray of two populations, namely larger particles unable to transverse baffles and smaller particles that are able to enter the lung, and for introducing said spray into said first chamber;
   (c) inhalation means connected to said housing for communication with said first, second and third chambers for permitting the patient to inhale particulate laden spray residing within said housing and to exhale said particular-laden spray save for that retained within the patient's lungs in a direction toward said first, second and third chambers; and
   (d) reservoir means connected to said housing in communication with said second chamber for receiving, as the patient exhales, particulate-laden spray being generated by said nebulizing means.

2. An aerosol inhalation apparatus as defined in claim 1 in which said reservoir means comprises a flexible, inflatable reservoir bag.

3. An aerosol inhalation apparatus as defined in claim 1 in which said third chamber has an outlet port in communication with atmosphere and in which said apparatus further includes filtering means connected to said outlet port for filtering particulate matter from particulate-laden mist flowing through said outlet port.

4. An aerosol inhalation apparatus as defined in claim 1 in which said third chamber is provided with a breathing port and in which said inhalation and exhalation means comprises an elongated tubular breathing member having a proximal end connected to said breathing port.

5. An aerosol inhalation apparatus as defined in claim 1, including accessing means for accessing said nebulizing means to supply fluid medication thereto.

6. An apparatus as defined in claim 1 in which said first chamber includes a settling chamber and in which said housing further includes first baffle means disposed intermediate said settling chamber and said second chamber for impeding the flow of said larger particles toward said second chamber, whereby said larger particles will fall by force of gravity into said settling chamber for entrapment therein.

7. An apparatus as defined in claim 6 in which said housing further includes second baffle means disposed intermediate said settling chamber and said third chamber for impeding the flow of said larger particles toward said third chamber, whereby said larger particles will fall by fore of gravity into said settling chamber for entrapment therein.

8. An aerosol inhalation apparatus for delivering a medicament containing mist to a patient comprising:

(a) a housing consisting essentially of interconnected first, second and third chambers, said first chamber including a settling chamber and being in free communication with said second and third chambers, said free communication being unobstructed by one-way check valves;

(b) nebulizing means connected to said housing for communication with said first chamber thereof for nebulizing a fluid medication containing the medicament to produce a particulate laden spray having a population of larder and smaller particles of medicament said smaller particles being capable of entering and penetrating the lungs of the patient, and for introducing said spray into said first chamber;

(c) inhalation means connected to said housing for communication with said first, second and third chambers for permitting the patient to inhale particulate laden spray residing within said housing and to exhale all of said particulate laden spray save that retained within the lungs of the patient; and (d) reservoir means connected to said housing in communication with said second chamber for receiving, as the patient exhales, particulate-laden spray being generated by said nebulizing means, said reservoir means comprising a flexible, inflatable reservoir bag.

9. An apparatus as defined in claim 8 in which said housing further includes a wall having an opening therein, said wall being disposed intermediate said settling chamber and said second chamber for impeding the flow of said larger particles toward said second chamber, whereby said particles will fall by force of gravity into said settling chamber for entrapment therein.

10. An apparatus as defined in claim 9 in which said housing further includes second baffle means disposed intermediate said settling chamber and said third chamber for impeding the flow of large particles toward said third chamber, whereby said large particles will fall by force of gravity into said settling chamber for entrapment therein.

11. An aerosol inhalation apparatus as defined in claim 9 in which said third chamber has an outlet port in communication with atmosphere and in which said apparatus further includes an apertured cap connected to said outlet port for impeding fluid flow through said outlet port.

12. An aerosol inhalation apparatus for delivering a medicament containing mist to a patient comprising:

(a) a housing consisting essentially of:
  (i) a first chamber having a settling chamber;
  (ii) a second chamber in communication with said first chamber;
  (iii) a first wall disposed immediate said first and second chambers;
  (iv) a third chamber in communication with said first chamber and including an outlet portion in communication with atmospheres said third chamber being in free communication with said first chamber, said communication being unobstructed by a one-way check valve;
  (v) a second wall disposed intermediate said first and third chambers;

(b) nebulizing means connected to said housing for communication with said first chamber thereof for nebulizing a fluid medication containing the medicament to produce a particulate laden spray having larger and smaller particles of medicament and for introducing said spray into said first chamber;

(c) inhalation and exhalation means connected to said housing for communication with said third chamber for permitting the patient to inhale particulate laden spray residing within said housing and to exhale into said first, second and third chambers all of said particulate laden spray save that residing within the patient's lungs;

(d) reservoir means connected to said housing in communication with said second chamber for receiving particulate-laden spray as the patient exhales, said reservoir means comprising a flexible, inflatable reservoir bag; and (e) means connected to said housing for impeding the flow of fluid from said third chamber through said outlet port.

* * * * *